United States Patent
Augeri et al.

(10) Patent No.: US 7,598,280 B2
(45) Date of Patent: Oct. 6, 2009

(54) HETEROCYCLIC COMPOUNDS, COMPOSITIONS COMPRISING THEM AND METHODS OF THEIR USE

(75) Inventors: David J. Augeri, Princeton, NJ (US); Jeffrey Bagdanoff, Robbinsville, NJ (US); Simon D. P. Baugh, Ringoes, NJ (US); Kenneth G. Carson, Princeton, NJ (US); Theodore C. Jessop, Lawrenceville, NJ (US); James E. Tarver, Morrisville, PA (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 12/038,872

(22) Filed: Feb. 28, 2008

(65) Prior Publication Data
US 2009/0030050 A1    Jan. 29, 2009

Related U.S. Application Data

(60) Provisional application No. 60/904,357, filed on Mar. 1, 2007.

(51) Int. Cl.
*C07D 277/20*    (2006.01)
*C07D 261/06*    (2006.01)
*C07D 249/14*    (2006.01)
*C07D 261/04*    (2006.01)
*C07D 403/04*    (2006.01)
*A61K 31/426*    (2006.01)
*A61K 31/422*    (2006.01)
*A61K 31/4178*   (2006.01)

(52) U.S. Cl. ......... 514/365; 548/205; 548/243; 548/247; 548/266.2; 548/313.4; 514/378; 514/383; 514/397

(58) Field of Classification Search .......... None
See application file for complete search history.

(56) References Cited

FOREIGN PATENT DOCUMENTS

WO    WO 2006/097030    *    9/2006

* cited by examiner

*Primary Examiner*—Joseph K. McKane
*Assistant Examiner*—Alicia L Fierro
(74) *Attorney, Agent, or Firm*—Max Bachrach

(57) ABSTRACT

Heterocyclic compounds, compositions comprising them, and methods of their use for the treatment, prevention and management of inflammatory and autoimmune diseases and disorders are disclosed. Particular compounds are of formula I:

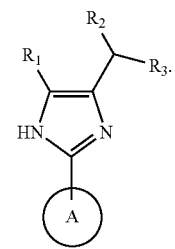

Figure 1:
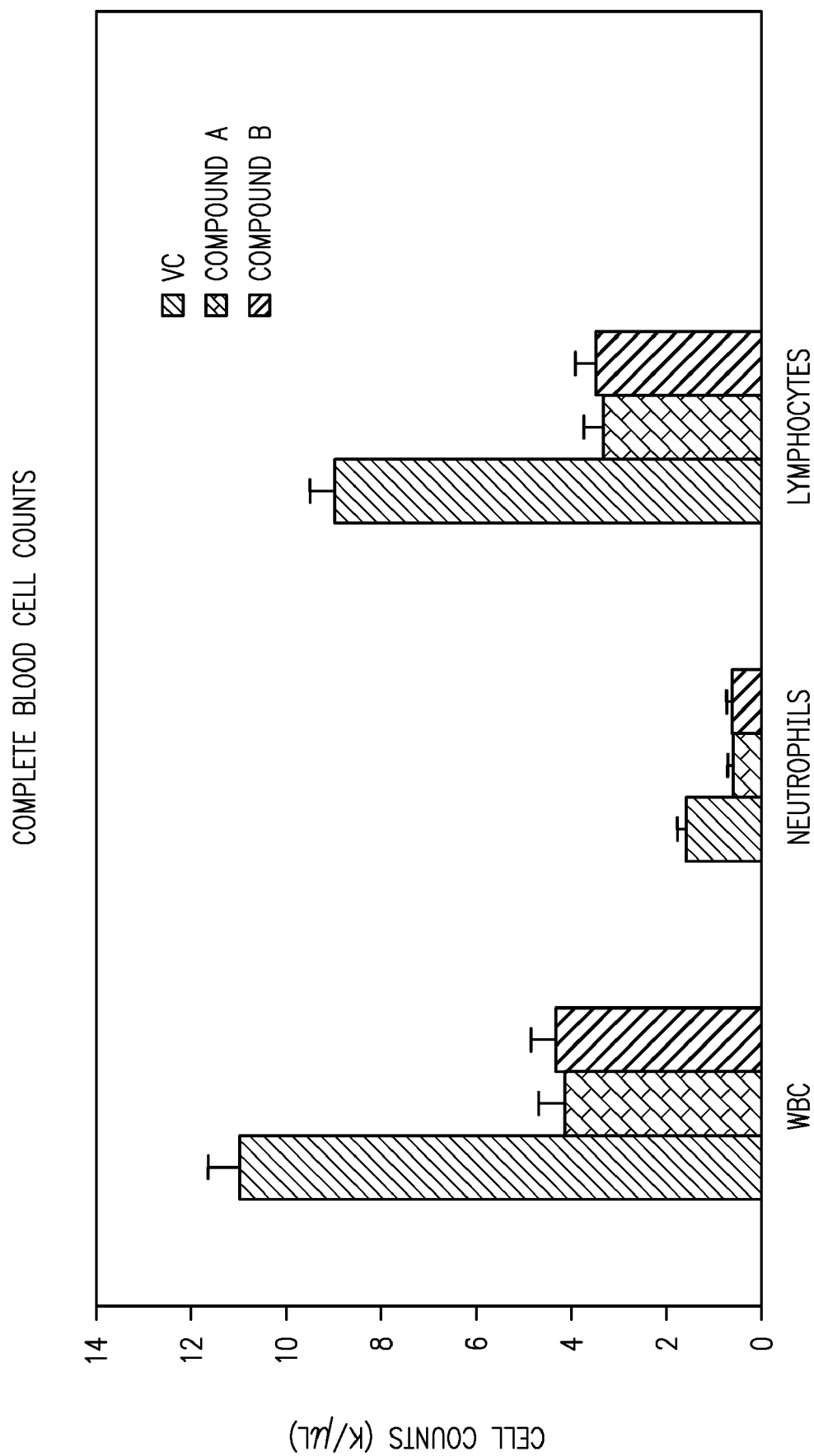

2 Claims, 1 Drawing Sheet

HETEROCYCLIC COMPOUNDS, COMPOSITIONS COMPRISING THEM AND METHODS OF THEIR USE

This application claims priority to U.S. provisional application No. 60/904,357, filed Mar. 1, 2007, the entirety of which is incorporated herein by reference.

1. FIELD OF THE INVENTION

This invention relates to imidazole-based compounds, and methods of their use for the treatment, prevention and management of various diseases and disorders.

2. BACKGROUND

Sphingosine-1-phosphate (S1P) is a bioactive molecule with potent effects on multiple organ systems. Saba, J. D. and Hla, T. *Circ. Res.* 94:724-734 (2004). Although some believe the compound is an intracellular secondary messenger, its mode of action is still a subject of debate. Id. Indeed, even its metabolism is poorly understood. Hla, T., *Science* 309:1682-3 (2005). Researchers currently believe that S1P is formed by the phosphorylation of sphingosine, and degraded by dephosphorylation or cleavage. Its cleavage into ethanolamine phosphate and a long-chain aldehyde is reportedly catalyzed by S1P lyase. Id.; Pyne & Pyne, *Biochem J.* 349: 385-402 (2000).

Sphingosine-1-phosphate lyase is a vitamin $B_6$-dependent enzyme localized in the membrane of the endoplasmic reticulum. Van Veldhoven and Mannaerts, *J. Biol. Chem.* 266: 12502-12507 (1991); Van Veldhoven and Mannaerts, *Adv. Lipid. Res.* 26:69 (1993). The polynucleotide and amino acid sequences of human SP1 lyase and its gene products are described in PCT Patent Application No. WO 99/16888.

Recently, Schwab and coworkers concluded that a component of caramel color III, 2-acetyl-4-tetrahydroxybutylimidazole (THI), inhibits S1P lyase activity when administered to mice. Schwab, S. et al, *Science* 309:1735-1739 (2005). While others have postulated that THI exerts its effects by a different mechanism (see, e.g., Pyne, S. G., *ACGC Chem. Res. Comm.* 11:108-112 (2000)), it is clear that administration of the compound to rats and mice induces lymphopenia and causes the accumulation of mature T cells in the thymus. See, e.g., Schwab, supra; Pyne, S. G., *ACGC Chem. Res. Comm.* 11:108-112 (2000); Gugsyan, R., et al., *Immunology* 93(3): 398-404 (1998); Halweg, K. M. and Büchi, G., *J. Org. Chem.* 50:1134-1136 (1985); U.S. Pat. No. 4,567,194 to Kroeplien and Rosdorfer. Still, there are no known reports of THI having an immunological effect in animals other than mice and rats. Although U.S. Pat. No. 4,567,194 alleges that THI and some related compounds may be useful as immunosuppressive medicinal agents, studies of the compound in humans found no immunological effects. See Thuvander, A. and Oskarsson, A., *Fd. Chem. Toxic.* 32(1):7-13 (1994); Houben, G. F., et al., *Fd. Chem. Toxic.* 30(9):749-757 (1992).

3. SUMMARY OF THE INVENTION

This invention is directed, in part, to compounds of formula I:

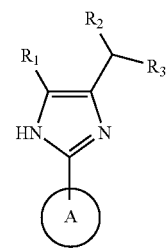

and pharmaceutically acceptable salts and solvates (e.g., hydrates) thereof, wherein: A is an optionally substituted heterocycle; $R_1$ is $OR_{1A}$, $OC(O)R_{1A}$, $C(O)OR_{1A}$, hydrogen, halogen, nitrile, or optionally substituted alkyl, aryl, alkylaryl, arylalkyl, heteroalkyl, heterocycle, alkylheterocycle, or heterocyclealkyl; $R_2$ is $OR_{2A}$, $OC(O)R_{2A}$, hydrogen, halogen, or optionally substituted alkyl, aryl, alkylaryl, arylalkyl, heteroalkyl, heterocycle, alkylheterocycle, or heterocyclealkyl; $R_3$ is $N(R_{3A})_2$, hydrogen, hydroxy, or optionally substituted alkyl, aryl, alkylaryl, arylalkyl, heteroalkyl, heterocycle, alkylheterocycle, or heterocyclealkyl; and each of $R_{1A}$, $R_{2A}$, and $R_{3A}$ is independently hydrogen or optionally substituted alkyl, aryl, alkylaryl, arylalkyl, heteroalkyl, heterocycle, alkylheterocycle, or heterocyclealkyl.

This invention also encompasses pharmaceutical compositions comprising compounds of formula I, and methods of treating inflammatory diseases and disorders using compounds of formula I.

4. BRIEF DESCRIPTION OF THE FIGURE

Certain aspects of this invention can be understood with reference to FIG. 1, which shows the effect of two compounds of the invention on the number of white blood cells (WBC), neutrophils and lymphocytes as measured 18 hours after oral dosing at 100 mpk as compared to a vehicle control (VC).

5. DETAILED DESCRIPTION

This invention is directed, in part, to compounds believed to be useful in the treatment, prevention and/or management of autoimmune and inflammatory diseases and disorders. The invention results from research prompted, in part, by studies of S1P lyase knockout mice. See U.S. patent application Ser. No. 11/698,253, filed Jan. 25, 2007.

5.1. DEFINITIONS

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "alkoxy" means an —O-alkyl group. Examples of alkoxy groups include, but are not limited to, —$OCH_3$, —$OCH_2CH_3$, —$O(CH_2)_2CH_3$, —$O(CH_2)_3CH_3$, —$O(CH_2)_4CH_3$, and —$O(CH_2)_5CH_3$.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the term "circulating lymphocyte reduction agent" means a compound that has a CLRF of greater than about 20 percent.

Unless otherwise indicated, the term "circulating lymphocyte reduction factor" or "CLRF" means the decrease in the number of circulating lymphocytes in mice caused by oral administration of a single dose of a compound at 100 mg/kg, as determined by the method described in the Examples, below.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "S1P level enhancing agent" means a compound that has a SLEF of at least about 10-fold.

Unless otherwise indicated, the term "S1P level enhancing factor" or "SLEF" means the increase in S1P in the spleens of mice caused by oral administration of a single dose of a compound at 100 mg/kg, as determined by the method described in the Examples, below.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehylde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. COMPOUNDS

This invention encompasses compounds of formula I:

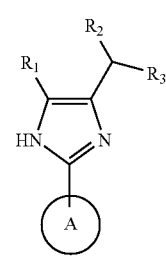

I and pharmaceutically acceptable salts and solvates (e.g., hydrates) thereof, wherein: A is an optionally substituted heterocycle; $R_1$ is $OR_{1A}$, $OC(O)R_{1A}$, $C(O)OR_{1A}$, hydrogen, halogen, nitrile, or optionally substituted alkyl, aryl, alkylaryl, arylalkyl, heteroalkyl, heterocycle, alkylheterocycle, or heterocyclealkyl; $R_2$ is $OR_{2A}$, $OC(O)R_{2A}$, hydrogen, halogen, or optionally substituted alkyl, aryl, alkylaryl, arylalkyl, heteroalkyl, heterocycle, alkylheterocycle, or heterocyclealkyl; $R_3$ is $N(R_{3A})_2$, hydrogen, hydroxy, or optionally substituted alkyl, aryl, alkylaryl, arylalkyl, heteroalkyl, heterocycle, alkylheterocycle, or heterocyclealkyl; and each of $R_{1A}$, $R_{2A}$, and $R_{3A}$ is independently hydrogen or optionally substituted alkyl, aryl, alkylaryl, arylalkyl, heteroalkyl, heterocycle, alkylheterocycle, or heterocyclealkyl.

Particular compounds are of formula I(a) or I(b):

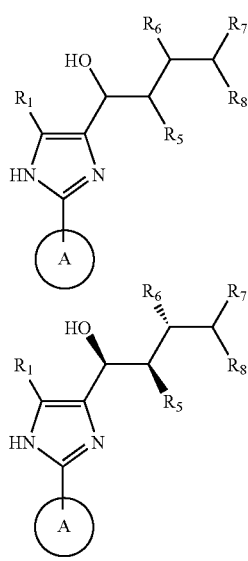

wherein: $R_5$ is $OR_{5A}$, $OC(O)R_{5A}$, $N(R_{5B})_2$, $NHC(O)R_{5B}$, hydrogen, or halogen; $R_6$ is $OR_{6A}$, $OC(O)R_{6A}$, $N(R_{6B})_2$, $NHC(O)R_{6B}$, hydrogen, or halogen; $R_7$ is $OR_{7A}$, $OC(O)R_{7A}$, $N(R_{7B})_2$, $NHC(O)R_{7B}$, hydrogen, or halogen; $R_8$ is $CH_2OR_{8A}$, $CH_2OC(O)R_{8A}$, $N(R_{8B})_2$, $NHC(O)R_{8B}$, hydrogen, or halogen; each of $R_{1A}$, $R_{5A}$, $R_{6A}$, $R_{7A}$, and $R_{8A}$ is independently hydrogen or optionally substituted alkyl, aryl, alkylaryl, arylalkyl, heteroalkyl, heterocycle, alkylheterocycle, or heterocyclealkyl; and each of $R_{5B}$, $R_{6B}$, $R_{7B}$ and $R_{8B}$ is independently hydrogen or alkyl optionally substituted with one or more hydroxy or halogen groups.

One embodiment of the invention encompasses compounds of formula II:

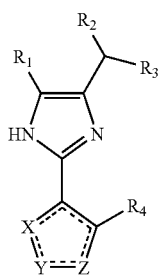

and pharmaceutically acceptable salts and solvates thereof, wherein: X is $CR_4$, $CHR_4$, N, $NR_9$, O or S; Y is $CR_4$, $CHR_4$, N, $NR_9$, O or S; Z is $CR_4$, $CHR_4$, N, $NR_9$, O or S; $R_1$ is $OR_{1A}$, $C(O)OR_{1A}$, hydrogen, halogen, nitrile, or optionally substituted alkyl, aryl, alkylaryl, arylalkyl, heteroalkyl, heterocycle, alkylheterocycle, or heterocyclealkyl; $R_2$ is $OR_{2A}$, $OC(O)R_{2A}$, hydrogen, halogen, or optionally substituted alkyl, aryl, alkylaryl, arylalkyl, heteroalkyl, heterocycle, alkylheterocycle, or heterocyclealkyl; $R_3$ is $N(R_{3A})_2$, hydrogen, hydroxy, or optionally substituted alkyl, aryl, alkylaryl, arylalkyl, heteroalkyl, heterocycle, alkylheterocycle, or heterocyclealkyl; each of $R_{1A}$, $R_{2A}$, and $R_{3A}$ is independently hydrogen or optionally substituted alkyl, aryl, alkylaryl, arylalkyl, heteroalkyl, heterocycle, alkylheterocycle, or heterocyclealkyl; each $R_4$ is independently $OR_{4A}$, $OC(O)R_{4A}$, hydrogen, halogen, or optionally substituted alkyl, aryl, alkylaryl, arylalkyl, heteroalkyl, heterocycle, alkylheterocycle, or heterocyclealkyl; each $R_9$ is independently hydrogen or optionally substituted alkyl, aryl, alkylaryl, arylalkyl, heteroalkyl, heterocycle, alkylheterocycle, or heterocyclealkyl; and each of $R_{1A}$, $R_{2A}$, $R_{3A}$ and $R_{4A}$ is independently hydrogen or optionally substituted alkyl, aryl, alkylaryl, arylalkyl, heteroalkyl, heterocycle, alkylheterocycle, or heterocyclealkyl.

Particular compounds are of formulae II(a) or II(b):

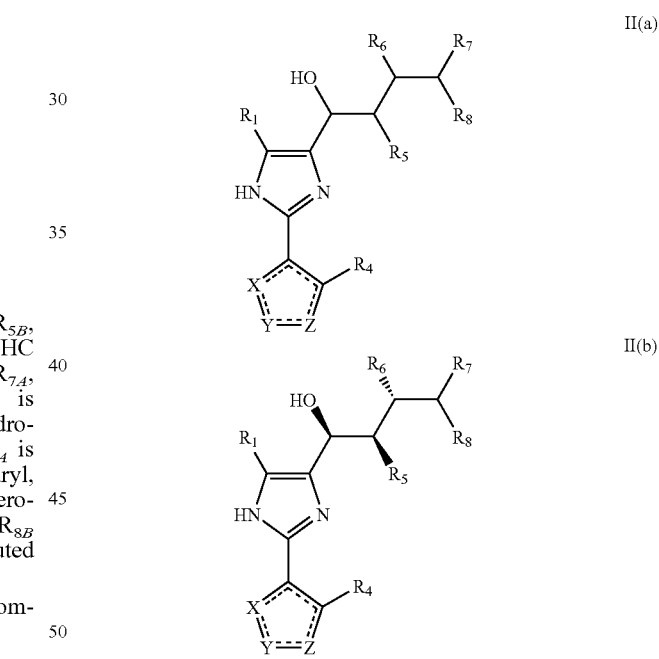

wherein: $R_5$ is $OR_{5A}$, $OC(O)R_{5A}$, $N(R_{5B})_2$, $NHC(O)R_{5B}$, hydrogen, or halogen; $R_6$ is $OR_{6A}$, $OC(O)R_{6A}$, $N(R_{6B})_2$, $NHC(O)R_{6B}$, hydrogen, or halogen; $R_7$ is $OR_{7A}$, $OC(O)R_{7A}$, $N(R_{7B})_2$, $NHC(O)R_{7B}$, hydrogen, or halogen; $R_8$ is $CH_2OR_{8A}$, $CH_2OC(O)R_{8A}$, $N(R_{8B})_2$, $NHC(O)R_{8B}$, hydrogen, or halogen; each of $R_{1A}$, $R_{5A}$, $R_{6A}$, $R_{7A}$, and $R_{8A}$ is independently hydrogen or optionally substituted alkyl, aryl, alkylaryl, arylalkyl, heteroalkyl, heterocycle, alkylheterocycle, or heterocyclealkyl; and each of $R_{5B}$, $R_{6B}$, $R_{7B}$ and $R_{8B}$ is independently hydrogen or alkyl optionally substituted with one or more hydroxy or halogen groups.

Another embodiment encompasses compounds of formula III:

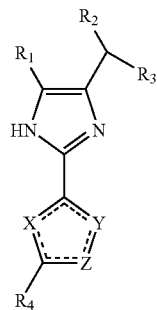

III and pharmaceutically acceptable salts and solvates thereof, wherein: X is $CR_4$, $CHR_4$, N, $NR_9$, O or S; Y is $CR_4$, $CHR_4$, N, $NR_9$, O or S; Z is $CR_4$, $CHR_4$, N, $NR_9$, O or S; $R_1$ is $OR_{1A}$, $C(O)OR_{1A}$, hydrogen, halogen, nitrile, or optionally substituted alkyl, aryl, alkylaryl, arylalkyl, heteroalkyl, heterocycle, alkylheterocycle, or heterocyclealkyl; $R_2$ is $OR_{2A}$, $OC(O)R_{2A}$, hydrogen, halogen, or optionally substituted alkyl, aryl, alkylaryl, arylalkyl, heteroalkyl, heterocycle, alkylheterocycle, or heterocyclealkyl; $R_3$ is $N(R_{3A})_2$, hydrogen, hydroxy, or optionally substituted alkyl, aryl, alkylaryl, arylalkyl, heteroalkyl, heterocycle, alkylheterocycle, or heterocyclealkyl; each of $R_{1A}$, $R_{2A}$, and $R_{3A}$ is independently hydrogen or optionally substituted alkyl, aryl, alkylaryl, arylalkyl, heteroalkyl, heterocycle, alkylheterocycle, or heterocyclealkyl; each $R_4$ is independently $OR_{4A}$, $OC(O)R_{4A}$, hydrogen, halogen, or optionally substituted alkyl, aryl, alkylaryl, arylalkyl, heteroalkyl, heterocycle, alkylheterocycle, or heterocyclealkyl; each $R_9$ is independently hydrogen or optionally substituted alkyl, aryl, alkylaryl, arylalkyl, heteroalkyl, heterocycle, alkylheterocycle, or heterocyclealkyl; and each of $R_{1A}$, $R_{2A}$, $R_{3A}$ and $R_{4A}$ is independently hydrogen or optionally substituted alkyl, aryl, alkylaryl, arylalkyl, heteroalkyl, heterocycle, alkylheterocycle, or heterocyclealkyl.

Particular compounds are of formulae III(a) or III(b):

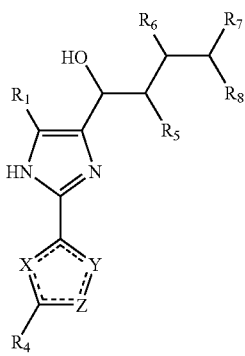

III(a)

-continued

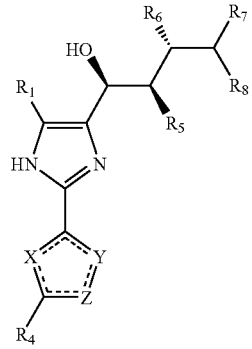

III(b)

wherein: $R_5$ is $OR_{5A}$, $OC(O)R_{5A}$, $N(R_{5B})_2$, $NHC(O)R_{5B}$, hydrogen, or halogen; $R_6$ is $OR_{6A}$, $OC(O)R_{6A}$, $N(R_{6B})_2$, $NHC(O)R_{6B}$, hydrogen, or halogen; $R_7$ is $OR_{7A}$, $OC(O)R_{7A}$, $N(R_{7B})_2$, $NHC(O)R_{7B}$, hydrogen, or halogen; $R_8$ is $CH_2OR_{8A}$, $CH_2OC(O)R_{8A}$, $N(R_{8B})_2$, $NHC(O)R_{8B}$, hydrogen, or halogen; each of $R_{1A}$, $R_{5A}$, $R_{6A}$, $R_{7A}$, and $R_{8A}$ is independently hydrogen or optionally substituted alkyl, aryl, alkylaryl, arylalkyl, heteroalkyl, heterocycle, alkylheterocycle, or heterocyclealkyl; and each of $R_{5B}$, $R_{6B}$, $R_{7B}$ and $R_{8B}$ is independently hydrogen or alkyl optionally substituted with one or more hydroxy or halogen groups.

Referring to the various formulae disclosed herein (e.g., formulae I, II and III), as applicable, in some compounds of the invention, A is a 5-membered optionally substituted heterocycle. Examples include optionally substituted dihydro-imidazole, dihydro-isoxazole, dihydro-pyrazole, dihydro-thiazole, dioxolane, dithiolane, dithiole, imidazole, isoxazole, isoxazolidine, oxathiolane, and pyrazole. In one embodiment, A is not optionally substituted furan, thiophene or pyrrole.

In some compounds, A is a 6-membered optionally substituted heterocycle (e.g., pyrimidine).

In some, X is $CR_4$ or $CHR_4$. In some, X is N or $NR_9$. In some, X is O or S.

In some, Y is $CR_4$ or $CHR_4$. In some, Y is N or $NR_9$. In some, Y is O or S.

In some, Z is $CR_4$ or $CHR_4$. In some, Z is N or $NR_9$. In some, Z is O or S.

In some, X is N and Y is O. In some, X is N and Y is $NR_9$. In some, X is N and Y is S. In some, X is N and Z is O. In some, X is N and Z is $NR_9$. In some, X is N and Z is S. In some, X is N, Y is N, and Z is $NR_9$.

In some, $R_1$ is hydrogen. In some, $R_1$ is nitrile. In some, $R_1$ is optionally substituted lower alkyl. In some, $R_1$ is $OR_{1A}$ or $C(O)OR_{1A}$ and $R_{1A}$ is, for example, hydrogen or optionally substituted lower alkyl.

In some, $R_2$ is $OR_{2A}$. In some, $R_2$ is $OC(O)R_{2A}$ and $R_{2A}$ is, for example, hydrogen. In some, $R_2$ is halogen.

In some, $R_3$ is optionally substituted alkyl (e.g., alkyl substituted with one or more halogen or $OR_{3A}$ moieties, wherein $R_{3A}$ is, for example, hydrogen or acetate). In some, $R_3$ is hydrogen. In some, $R_3$ is hydroxyl. In some, $R_3$ is optionally substituted heteroalkyl (e.g., alkoxy). In some, $R_3$ is heteroalkyl substituted with one or more halogen, hydroxyl or acetate.

In some, $R_4$ is hydrogen or optionally substituted alkyl, aryl or alkylaryl.

In some, each of $R_5$, $R_6$, $R_7$, and $R_8$ is hydrogen or halogen. In some, one or more of $R_5$, $R_6$, $R_7$, and $R_8$ is hydroxyl or acetate. In some, all of $R_5$, $R_6$, $R_7$, and $R_8$ are hydroxyl.

In some, $R_9$ is hydrogen or optionally substituted alkyl, aryl or alkylaryl.

Compounds of the invention may contain one or more stereocenters, and can exist as racemic mixtures of enantiomers or mixtures of diastereomers. This invention encompasses stereomerically pure forms of such compounds, as well as mixtures of those forms. Stereoisomers may be asymmetrically synthesized or resolved using standard techniques such as chiral columns or chiral resolving agents. See, e.g., Jacques, J., et al, *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions*, p. 268 (E. L. Eliel, Ed., Univ. of Notre Dame Press, Notre Dame, Ind., 1972).

This invention further encompasses stereoisomeric mixtures of compounds disclosed herein. It also encompasses configurational isomers of compounds disclosed herein, either in admixture or in pure or substantially pure form, such as cis (Z) and trans (E) alkene isomers and syn and anti oxime isomers.

Preferred compounds of the invention are circulating lymphocyte reduction agents. Certain compounds inhibit the amount of circulating lymphocytes, as determined using the method described in the Examples, by greater than about 20, 50, 75, 100, 150 or 200 percent. In this regard, it has been found that while THI is capable of reducing circulating lymphocytes in mice, many analogues and derivatives of THI, such as 1-(4-methyl-5-((1S,2R,3R)-1,2,3,4-tetrahydroxybutyl)thiazol-2-yl)ethanone, have little or no effect on circulating lymphocytes, despite reports to the contrary. See WO 97/46543.

Without being limited by theory, compounds of the invention are believed to affect the S1P metabolic pathway, and may inhibit S1P lyase directly or indirectly in vivo. Particular compounds are S1P level enhancing agents. Certain compounds increase the amount of S1P, as determined using the method described below in the Examples, by greater than about 10, 15, 20, 25, or 30-fold.

Compounds of the invention can be prepared by methods known in the art (e.g., by varying and adding to the approaches described in Pyne, S. G., *ACGC Chem. Res. Comm.* 11:108-112 (2000); Halweg, K. M. and Büchi, G., *J. Org. Chem.* 50:1134-1136 (1985)). Compounds can also be made by the methods disclosed below and variants thereof, which will be apparent to those of ordinary skill in the art.

For example, compounds of formula I can be prepared from commercially available, and/or readily prepared nitriles, as shown below:

Scheme 1

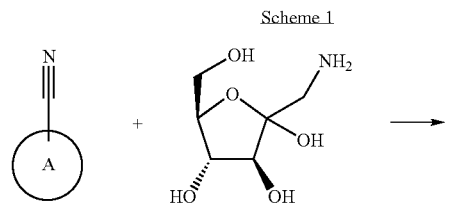

-continued

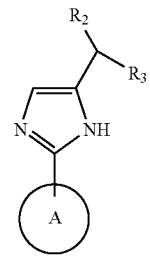

wherein, for example, the reactants are combined with one equivalent of NaOMe in MeOH at room temperature, followed by the addition of acid (e.g., aqueous HCl).

5.3. METHODS OF USE

This invention encompasses a method of modulating (e.g., increasing) the amount of S1P in a patient (e.g., a mouse, rat, dog, cat or human) in need thereof, which comprises administering to the patient an effective amount of a compound of the invention (i.e., a compound disclosed herein).

Another embodiment encompasses a method of reducing the number of T-cells in the blood of a patient, which comprises administering to the patient an effective amount of a compound of the invention.

Another embodiment encompasses a method of treating, managing or preventing a disease affected by (or having symptoms affected by) S1P levels, which comprises administering to a patient in need thereof a therapeutically or prophylactically effective amount of a compound of the invention.

Another embodiment encompasses a method of suppressing immune response in a patient, which comprises administering to the patient an effective amount of a compound of the invention.

Another embodiment encompasses a method of treating, managing or preventing an autoimmune or inflammatory disease or disorder, which comprises administering to a patient in need thereof a therapeutically or prophylactically effective amount of a compound of the invention. Examples of diseases and disorders include ankylosing spondylitis, asthma (e.g., bronchial asthma), atopic dermatitis, Behcet's disease, graft-vs-host disease, Kawasaki syndrome, lupus erythematosus, multiple sclerosis, myasthenia gravis, pollinosis, psoriasis, psoriatic arthritis, rheumatoid arthritis, scleroderma, transplant rejection (e.g., of organ, cell or bone marrow), type 1 diabetes, and uveitis.

Additional diseases and disorders include Addison's Disease, anti-phospholipid syndrome, autoimmune atrophic gastritis, achlorhydra autoimmune, Celiac Disease, Crohn's Disease, Cushing's Syndrome, dermatomyositis, Goodpasture's Syndrome, Grave's Disease, Hashimoto's thyroiditis, idiopathic adrenal atrophy, idiopathic thrombocytopenia, Lambert-Eaton Syndrome, pemphigoid, pemphigus vulgaris, pernicious anemia, polyarteritis nodosa, primary biliary cirrhosis, primary sclerosing cholangitis, Raynauds, Reiter's Syndrome, relapsing polychondritis, Schmidt's Syndrome, Sjogren's Syndrome, sympathetic ophthalmia, Takayasu's Arteritis, temporal arteritis, thyrotoxicosis, ulcerative colitis, and Wegener's granulomatosis.

The amount, route of administration and dosing schedule of a compound will depend upon factors such as the specific indication to be treated, prevented, or managed, and the age, sex and condition of the patient. The roles played by such factors are well known in the art, and may be accommodated by routine experimentation. In a particular embodiment, a compound of the invention is administered to a human patient in an amount of about 0.5, 1, 2.5 or 5 mpk.

5.4. PHARMACEUTICAL FORMULATIONS

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin, β-cyclodextrin, Captisol™, and Encapsin™ (see, e.g., Davis and Brewster, 2004, *Nat. Rev. Drug Disc.* 3:1023-1034), Labrasol®, Labrafil®, Labrafac®, cremafor, and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:cornoil).

Poorly soluble compounds may also be incorporated into suspensions using other techniques known in the art. For example, nanoparticles of a compound may be suspended in a liquid to provide a nanosuspension (see, e.g., Rabinow, 2004, *Nature Rev. Drug Disc.* 3:785-796). Nanoparticle forms of compounds described herein may be prepared by the methods described in U.S. Patent Publication Nos. 2004-0164194, 2004-0195413, 2004-0251332, 2005-0042177 A1, 2005-0031691 A1, and U.S. Pat. Nos. 5,145,684, 5,510,118, 5,518,187, 5,534,270, 5,543,133, 5,662,883, 5,665,331, 5,718,388, 5,718,919, 5,834,025, 5,862,999, 6,431,478, 6,742,734, 6,745,962, the entireties of each of which are incorporated herein by reference. In one embodiment, the nanoparticle form comprises particles having an average particle size of less than about 2000 nm, less than about 1000 nm, or less than about 500 nm.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

5.4.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences,* 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.4.2. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.4.3. Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

6. EXAMPLES

Aspects of this invention can be understood from the following examples, which do not limit its scope.

6.1. Synthesis of (1R,2S,3R)-1-(2-(5-methylisoxazol-3-yl)-1H-imidazol-5-yl)butane-1,2,3,4-tetraol

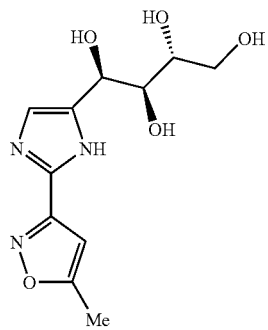

The captioned compound was prepared by General Method A, which is shown below in Scheme 2:

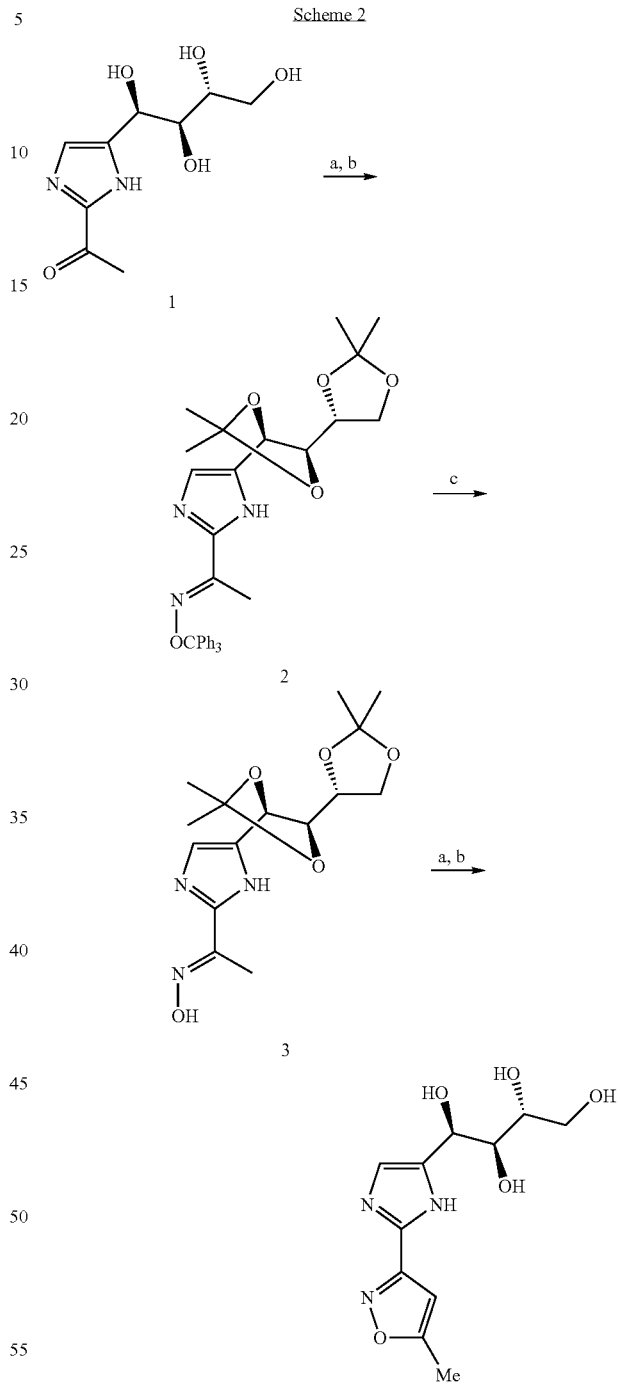

wherein: a is DCE:(MeO)$_2$CMe$_2$ (1:1), p-TsOH, 70° C.; b is Ph$_3$CONH$_2$, MeOH, 1N HCl (1.0 equiv.); c is 2 N HCl/dioxane; d is n-BuLi 4.0 equiv, THF, 0° C., then N-methyl-N-methoxyacetamide 5.0 equiv.; and e is 1N HCl:dioxane (1:1).

In particular, to a slurry of 1 (4.34 g, 18.87 mmol) in dichloromethane (30 ml) was added 2,2-dimethoxypropane (30 ml) followed by p-toluenesulfonic acid monohydrate (900 mgs, 4.72 mmol). The slurry was heated to 70° C. for 16 h, then cooled to room temperature, and treated with excess triethylamine (1 ml). The reaction was concentrated and dried by toluene azeotrope to give an amber solid that was carried on immediately without purification.

The amber solid was dissolved in MeOH (100 ml), and then treated with N-trityl hydroxylamine (6.75 g, 24.53 mmol) and 1N HCl (18.5 ml, 18.5 mmol). The reaction became clear after 1 h, and was maintained at room temperature for 18 h. At completion, the reaction was neutralized to pH=7 with 10N NaOH solution, then concentrated under reduced pressure. The crude material was purified by chromatography on silica gel (32-63 µm, 10% MeOH:$CH_2Cl_2$ w/1% $NH_4OH$) to provide the protected product 2 (9.8 g, 91% yield, 2 steps) as a white foam.

Anhydrous 4M dioxane (20 ml) was added to a solution of 2 (3.11 g, 5.48 mmol) in anhydrous dioxane (40 ml). After 1 h, the reaction was concentrated under vacuum, then redissolved in anhydrous DCM (60 ml), treated with excess triethylamine (5 ml), then concentrated again. The crude product was flashed over silica gel (3-8% MeOH:$CH_2Cl_2$ w/0.5-1.0% $NH_4OH$) to provide the oxime 3 (1.05 g, 59% yield) as a white foam.

To a −45° C. solution of 3 (500 mgs, 1.54 mmol) in THF (15 ml) was added dropwise a 1.6 M hexane solution of n-BuLi (3.85 ml, 6.16 mmol). After 10 min, N-methyl-N-methoxyacetamide (0.79 ml, 7.69 mmol) was added dropwise and the reaction was allowed to warm to room temperature. After 2 h, the reaction was quenched by addition of $NH_4Cl$ (10 ml) and diluted with water (5 ml) to dissolve solids. The layers were separated and the aqueous layer was extracted with $Et_2O$ (2×20 ml). The combined organics were washed with brine (25 ml), then dried over $MgSO_4$ and concentrated under vacuum. The resulting foam was purified by flash chromatography over silica gel (60-90% EtOAc:hexane) to provide a white foam solid.

To a solution of this intermediate white solid in dioxane (5 ml) was added 1N HCl (5 ml). The reaction was heated to 80° C. for 2 h, and then concentrated under reduced pressure to dryness. The resulting glassy solid was lyophilized from water (8 ml) to provide 4 (224 mgs, 48% yield, 2 steps) as a fluffy white powder. MS m/z $C_{11}H_{15}N_3O_5$ [M+H]$^+$=270; $^1$H NMR (400 MHz, $D_2O$): δ 7.54 (s, 1H), 6.7 (s, 1H), 5.2 (s, 1H), 3.83-3.59 (m, 4H), 2.49 (s, 1H); $^{13}$C NMR (100 MHz, $D_2O$): δ174.3, 150.0, 136.6, 135.0, 118.1, 101.0, 73.1, 71.0, 65.0, 63.2.

6.2. Synthesis of (1R,2S,3R)-1-(2-(5-ethylisoxazol-3-yl)-1H-imidazol-5-yl)butane-1,2,3,4-tetraol

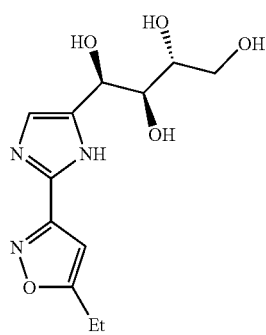

This compound was synthesized by General Method A, by alkylating intermediate 3 with N-methyl-N-methoxy ethyl amide. MS m/z $C_{12}H_{17}N_3O_5$ [M+H]$^+$=284; $^1$H NMR (400 MHz, $D_2O$): δ 7.24 (s, 1H), 6.54 (s, 1H), 4.95 (s, 1H), 3.84-3.56 (m, 4H), 2.82-2.77 (m, 2H), 1.25 (t, J=6.0 Hz, 3H).

6.3. Synthesis of (1R,2S,3R)-1-(2-(isoxazol-3-yl)-1H-imidazol-5-yl)butane-1,2,3,4-tetraol

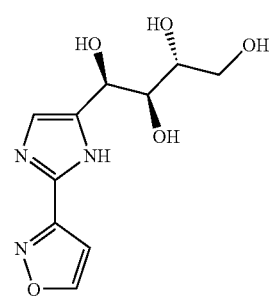

This compound was prepared by modifying General Method A as shown below in Scheme 3:

Scheme 3

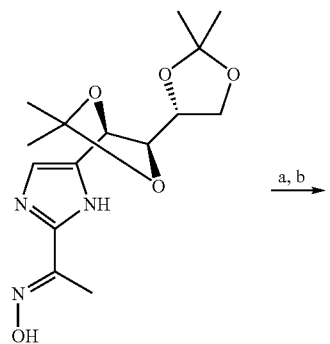

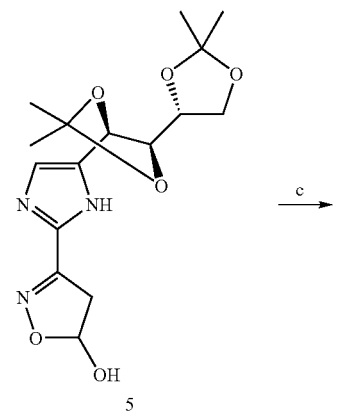

-continued

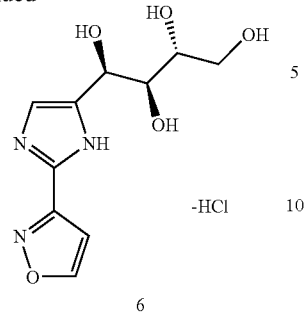

wherein: a is n-BuLi (4.0 equiv), THF, 0° C., then DMF (5.0 equiv.); b is TFAA, pyridine, DCM; and c is 1N HCl:dioxane (1:1), 50° C.

In particular, to a −45° C. solution of 3 (424 mgs, 1.30 mmol) in THF (15 ml) was added dropwise a 2.5 M hexane solution of n-BuLi (2.1 ml, 5.25 mmol). After 10 min, anhydrous DMF (0.505 ml, 6.52 mmol) was added dropwise and the reaction was allowed to warm to room temperature. After 2 h, the reaction was quenched by addition of NH$_4$Cl (10 ml) and diluted with water (5 ml) to dissolve solids. The layers were separated and the aqueous layer was washed with Et$_2$O (2×20 ml). The combined organics were washed with brine (25 ml), then dried over MgSO$_4$ and concentrated under vacuum. The resulting foam was flashed over silica gel (3-6% MeOH: CH$_2$Cl$_2$ with 0.5% NH$_4$OH) to provide the hemiacetal 5 (220 mgs, 47% yield) as a white foam.

To a 0° C. solution of 5 (130 mgs, 0.37 mmol) in THF was sequentially added pyridine (120 µl, 1.48 mmol) and trifluoroacetic acid anhydride. The reaction was warmed to room temperature for 10 min, and then heated to 55° C. for 16 h. At completion, the reaction was concentrated under vacuum, then purified by flash chromatography over silica gel (60-90% EtOAc:hexane) to provide the heterobicycle bisketal (60 mgs, 47% yield) as a white foam that was finally deprotected using standard acidic conditions to give Example 3 compound as a white crystalline solid. MS m/z C$_{10}$H$_{13}$N$_3$O$_5$ [M+H]$^+$=256; $^1$H NMR (400 MHz, D$_2$O) δ 8.87 (s, 1H), 7.55 (s, 1H), 7.05 (s, 1H), 5.21 (s, 1H), 3.75 (m, 3H), 3.63 (m, 2H).

6.4. Alternate Synthesis of (1R,2S,3R)-1-(2-(isoxazol-3-yl)-1H-imidazol-5-yl)butane-1,2,3,4-tetraol The captioned compound was also prepared by the approach referred to herein as General Method B, which is shown below in Scheme 4:

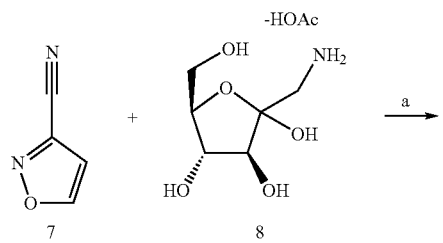

wherein: a is 1.0 equiv NaOMe in MeOH, at room temperature, then aq. HCl.

In particular, to a room temperature solution of the nitrile 7 (600 mgs, 6.38 mmol) in MeOH (10 ml) was added 25% w/v MeONa (0.83 ml, 3.83 mmol). After 3 h, fructosamine-acetate (1.53 g, 6.38 mmol) was added and the solution was maintained at room temperature with vigorous stirring for 5 h. Another portion of 25% w/v MeONa (0.66 ml, 3.19 mmol) was then added to the thick slurry. After 16 h, the reaction was filtered and the cake washed with cold MeOH. The cake was then treated with 1N HCl (20 ml) and filtered. The aqueous solution was concentrated under vacuum to constant weight to provide title compound (1.30 g, 66% yield) as a white powder.

6.5. Synthesis of (1R,2S,3R)-1-(2-(2-methylthiazol-4-yl)-1H-imidazol-4-yl)butane-1,2,3,4-tetraol

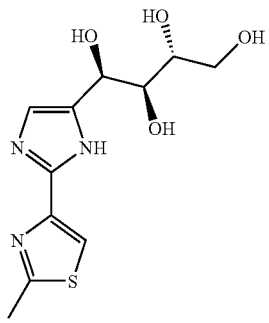

The title compound was prepared by General Method B using 2-methylthiazole-4-carbonitrile (1.023 g, 8.25 mmol), sodium methoxide in methanol (25 wt %, 1.07 ml, 4.95 mmol), methanol (8.25 ml) and compound 8 (2.00 g, 8.26 mmol). After 2.5 days, and additional portion of sodium methoxide in methanol (25 wt %, 0.891 ml, 4.125 mmol) was added. After 24 hours, the solid that had formed was collected by filtration and washed with cold methanol to afford the title compound (1.70 g, 5.96 mmol, 72% yield). MS m/z C$_{11}$H$_{15}$N$_3$O$_4$S [M+H]=286; $^1$H NMR (400 MHz, CD$_3$OD) δ 2.81 (s, 3H), 3.67-3.75 (m, 2H), 3.77-3.88 (m, 2H), 5.21 (s, 1H), 7.47 (s, 1H), 8.35 (s, 1H).

6.6. Synthesis of (1R,2S,3R)-1-(2-(1-benzyl-1H-1,2,4-triazol-3-yl)-1H-imidazol-4-yl)butane-1,2,3,4-tetraol Hydrochloride

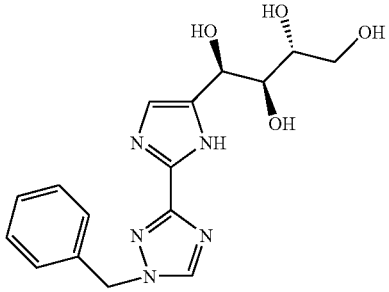

The captioned compound was prepared by General Method B with the following alterations: 1-benzyl-1H-1,2,4-triazole-3-carbonitrile (2.10 g, 11.4 mmol) was dissolved in methanol (12 ml) and treated with sodium methoxide in methanol (25 wt %, 1.48 ml, 6.8 mmol) and stirred for 18 h and 8 was added and the reaction stirred for 18 h. The resulting solid was isolated by filtration, washed with methanol and dried in vacuo to afford a white solid (3.20 g, 9.28 mmol, 81% yield). This solid was suspended in THF (50 ml), cooled in an ice bath and HCl (4 M in dioxane, 7.5 ml, 30 mmol) was added. The ice bath was removed and the suspension was stirred for 4 h. The solid was isolated by filtration, washed with THF and dried in vacuo to afford the title compound (3.50 g, 9.19 mmol, 99% yield) as a white solid. MS m/z $C_{16}H_{19}N_5O_4$ [M+H]+=346; $^1$H NMR (400 MHz, CD$_3$OD) δ 2.81 (s, 3H), 3.67-3.75 (m, 2H), 3.77-3.88 (m, 2H), 5.21 (s, 1H), 7.47 (s, 1H), 8.35 (s, 1H).

6.7. Synthesis of (1R,2S,3R)-1-(1H,1'H-2,2'-biimidazol-5-yl)butane-1,2,3,4-tetraol

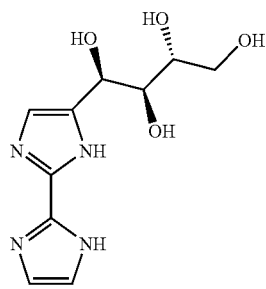

The captioned compound was prepared by General Method B with the following alterations. To a solution of 1H-imidazole-2-carbonitrile (0.39 g, 4.17 mmol) in methanol (4.8 ml) was added a solution of sodium methoxide in methanol (25 wt %, 0.54 g, 0.57 ml, 2.50 mmol), stirred for 16 h and compound 8 (0.964 g, 4.17 mmol) was added in 10 ml of MeOH. A precipitate formed and was filtered and washed with acetone (15 ml). The filtrate was concentrated to dryness, and was purified by preparative HPLC (10 mM aq ammonium acetate/acetonitrile) to give the title compound (0.0141 g, 0.0554 mmol) as an off-white solid. MS m/z $C_{10}H_{14}N_4O_4$ [M+H]+=255; $^1$H NMR (400 MHz, CD$_3$OD) δ 3.56-3.57 (m, 2H), 3.67-3.74 (m, 2H), 4.90 (s, 1H), 7.04 (s, 1H).

6.8. Synthesis of (1R,2S,3R)-1-(2-(5-methoxy-4,5-dihydroisoxazol-3-yl)-1H-imidazol-5-yl)butane-1,2,3,4-tetraol

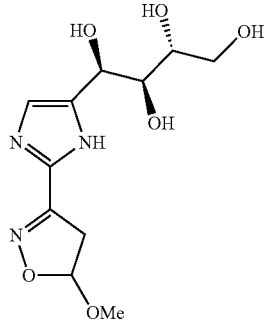

A 1M solution of HCl (10 ml) was added to a room temperature solution of the imidazole 5 (Scheme 3, 500 mg, 1.41 mmol) in MeOH (10 ml). The reaction was heated to 50° C. for 8 h, cooled to room temperature, and concentrated to dryness to provide the title compound (430 mgs, 100% yield) as a slightly yellow powder as a 1:1 mixture of diastereomers. MS m/z $C_{11}H_{17}N_3O_6$ [M+H]+=288; $^1$H NMR (400 MHz, D$_2$O) δ 7.06 (s, 1H), 5.71 (d, J=7.2 Hz) and 5.41 (d, J=7.2 Hz, 1H), 4.72 (s, 1H), 3.2-3.4 (m, 3H), 2.98-2.80 (m, 2H).

6.9. Synthesis of (1R,2S,3R)-1-(2-(5-methyl-1H-pyrazol-3-yl)-1H-imidazol-5-yl)butane-1,2,3,4-tetraol

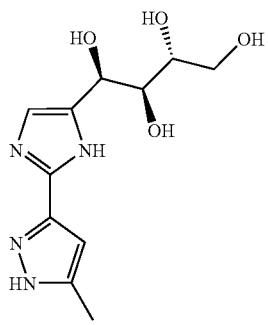

The title compound was prepared from 1-(5-((4S,4'R,5R)-2,2,2',2'-tetramethyl-4,4'-bi(1,3-dioxolan)-5-yl)-1H-imidazol-2-yl)ethanone (compound 9) as follows. A solution of 9 (975 mg, 3.15 mmol) in THF (15 ml) was added slowly to a −10° C. solution of potassium hexamethyldisilazane (15.72 ml of a 0.5 M toluene solution, 7.86 mmol) in THF (15 ml). The reaction was maintained at −10° C. for 10 min before the addition of ethyl acetate (1.55 ml, 15.75 mmol). The reaction was warmed to room temperature for 1 h, then quenched by the addition of 30 ml NH$_4$Cl (sat. aq.). The layers were separated, and the aqueous layer was washed with EtOAc (2×30 ml). The combined organics were washed with water (30 ml) and brine (30 ml), then dried over MgSO$_4$ and concentrated. The resulting tan material was used without further purification.

The crude material was dissolved in EtOH (20 ml) and acidified with 1N HCl (5 ml). The stirred, room temperature solution was then treated with excess hydrazine monohydrate (200 µl). At completion, the reaction was adjusted to pH=7 with 1 N NaOH, then concentrated to a 10 ml volume. DCM (30 ml) was added to dissolve the solids which had precipitated from the aqueous solution, and the layers were separated. The organic layer was dried over $MgSO_4$ and concentrated. The crude was flashed over silica (5-10% MeOH: DCM eluent) to provide the protected pyrazole (204 mg, 19% yield) as a clear foam.

A solution of 1N HCl (5 ml) was added to a room temperature solution of the protected heterobicycle (180 mgs, 0.52 mmol), and the reaction was heated to 50° C. After 1.5 h, the reaction was cooled to room temperature, then concentrated to dryness. The foam was re-dissolved in 2 ml MeOH, then triturated with 3 ml $Et_2O$ and cooled to 0° C. before decanting the liquids. The solid was washed with $Et_2O$ (2×2 ml), then dried under a high vacuum to provide the title compound (130 mgs, 70% yield) as a white powder. MS m/z $C_{16}H_{16}N_4O_4$ $[M+H]^+$=269; $^1H$ NMR (400 MHz, $D_2O$) δ 7.28 (s, 1H), 6.52 (s, 1H), 5.07 (d, J=0.9 Hz, 1H), 3.74-3.54 (m, 4H), 2.22 (s, 1H); $^{13}C$ NMR ($D_2O$): δ 142.8, 139.1, 136.3, 134.1, 116.0, 104.0, 72.6, 70.6, 64.4, 62.7, 9.6.

6.10. Measuring Effects on Lymphocytes in Mice

Compounds were administered by oral gavage or in drinking water. For oral dosing experiments, compounds were resuspended from crystals at 10 mg/ml in vehicle (e.g., water). Mice (F1 hybrids of 129/B6 strain) were gavaged with a single 100 mg/kg dose of compound (equivalent to 100 mpk of the free base for each compound) or a vehicle-only control, and returned to their cages. Mice were anesthetized using isofluorane eighteen hours after dosing and tissues were collected for analysis as described below. For drinking water studies, compounds were dissolved at 50 mg/L in acidified water (pH=2.8) containing 10 g/L glucose. The mice were allowed free access to compound-containing water (or glucose solution as a control) for 72 hours. At the end of 72 hours, tissues were collected for analysis.

CBC measurements were obtained as follows. Mice were anesthetized with isofluorane and blood was collected from the retroorbital plexus into EDTA blood collection tubes (Capiject-MQK, Terumo Medical Corp., Elkton, Md.). Automated CBC analysis was performed using a Cell-Dyn 3500 (Abbott Diagnostics, Abbott Park, Ill.) or a HemaVet 850 (Drew Scientific, Inc., Oxford, Conn.) instrument.

Flow cytometry (FACS) measurements were obtained as follows. Twenty five µl whole blood was lysed by hyoptonic shock, washed once in 2 ml FACS wash buffer (FWB: PBS/0.1% BSA/0.1% $NaN_3$/2 mM EDTA) and stained for 30 minutes at 4° C. in the dark with a combination of fluorochrome-conjugated antibodies diluted in 50 µl FWB. After staining, the cells were washed once with 2 ml FWB and resuspended in 300 µl FWB for acquisition.

Standard procedures for non-sterile removal of spleen and thymus were followed. Organs were dispersed into single-cell suspensions by forcing the tissue through a 70 µm cell strainer (Falcon, Becton Dickinson Labware, Bedford, Mass.). For FACS analysis, RBCs were lysed by hypotonic lysis, washed, and 1×10⁶ cells were incubated with 10 µl anti-CD16/CD32 (Fc Block™, BD-PharMingen, San Diego, Calif.) (1/10 dilution in FWB) for 15 minutes at 4° C. The cells were stained with a combination of fluorochrome-conjugated antibodies diluted in 50-100 µl FWB, added directly to the cells in Fc Block, for 30 minutes at 4° C. in the dark. After staining the cells were washed once with 1 ml FWB, and resuspended in 300 µl FWB for acquisition. All antibodies were purchased from BD-PharMingen, San Diego, Calif. unless otherwise specified. Samples were analyzed using a FACSCalibur flow cytometer and CellQuest Pro software (Becton Dickinson Immunocytometry Systems, San Jose, Calif.).

Antibody mixes used for the thymus were: TCRb APC Cy7; CD4 APC; CD8 PerCP; CD69 FITC; and CD62L PE1. Antibody mixes used for spleen and blood were: B220 PerCP; TCRb PC; CD4 APC Cy7; CD8 PE Cy7; CD69 FITC; and CD62L PE.

6.11. Measuring Effects on S1P Levels in Mice

Levels of S1P in mouse (F1 hybrids of 129/B6 strain) spleen are measured using an adaptation of the radio-receptor binding assay described in Murata, N., et al., *Anal. Biochem.* 282:115-120 (2000). This method utilizes HEK293F cells overexpressing Edg-1, one of the S1P receptor subtypes, and is based on the competition of labeled S1P with unlabeled S1P in a given sample.

HEK293F cells are transfected with a pEFneo S1P receptor (Edg-1)-expression vector and a G418-resistant cell clone is selected. The Edg-1-expressing HEK293F cells are cultured on 12 multiplates in DMEM containing 5% (v/v) FBS in a humidified air:$CO_2$ (19:1) atmosphere. Twenty four hours before the experiment, the medium is changed to fresh DMEM (without serum) containing 0.1% (w/v) BSA.

Eighteen hours after the test compound is administered, mice are sacrificed and their spleens are removed and frozen. S1P is obtained from the frozen tissue using known methods. See e.g., Yatomi, Y., et al, *FEBS Lett.* 404:173-174 (1997). In particular, 10 mouse spleens in 1 ml ice cold 50 mM phosphate buffer (pH 7.5) containing 1 mM EGTA, 1 mM DTT and Roche complete protease inhibitors are homogenized three times at one minute intervals on ice. The result is centrifuged at 2500 rpm and 4° C. for 10 minutes to remove cell debris. The supernatant is then ultracentrifuged at 45000 rpm and 4° C. in a 70Ti rotor for 1 hour to pull down the membrane-associated proteins. The supernatant is discarded, and the pellet is resuspended in minimal volume (~1 ml) of ice cold 50 mM phosphate buffer (pH 7.5) containing 1 mM EGTA, 1 mM DTT and 33% glycerol with Roche complete protease inhibitors present. The total protein concentration is measured using the Bradford assay.

S1P is extracted into chloroform/KCl/$NH_4OH$ (pH 12), and the upper aqueous phase is kept. It was then extracted in chloroform/methanol/HCl (pH<1), and the lower organic phase is kept and evaporated to provide S1P, which is stored in a freezer until used. Just before the assay, the dried sample is dissolved by sonication in a binder buffer consisting of 20 mM Tris-HCl (pH 7.5), 100 mM NaCl, 15 mM NaF, and 0.4% (w/v) BSA.

The S1P content of a sample is measured by a radioreceptor-binding assay based on a competitive binding of $[^{33}P]S1P$ with S1P in the sample on Edg-1-expressing cells. Edg-1-expressing HEK293F cells in confluent 12 multiplates are washed twice with the ice-cold binding buffer and then incubated with the same buffer containing 1 nM $[^{33}P]S1P$ (about 18.00 dpm per well) and increasing doses of authentic S1P or test sample in a final volume of 0.4 ml. The plates are kept on ice for 30 minutes, and the cells are washed twice with the same ice-cold binding buffer to remove unbound ligand. The cells are solubilized with a solution composed of 0.1% SDS, 0.4% NaOH, and 2% $Na_2CO_3$, and the radioactivity is counted by a liquid scintillation counter. The S1P content in the assay well is estimated by extrapolation from the standard displacement curve. The content of S1P in the initial test sample(s) is calculated by multiplying the value obtained from the standard curve by the recovery efficiency of S1P extraction and the dilution factor.

6.12. Compounds' Effects on Lymphocytes in Mice

Using the methods described above, the in vivo effects of various compounds were determined. The effects of two of the compounds as compared to vehicle controls are shown in FIG. 1. The compounds were administered to mice (F1 hybrids of 129/B6 strain) in drinking water. The results were obtained 18 hours after oral dosing of the compounds at 100 mpk.

All cited publications, patents, and patent applications are herein incorporated by reference in their entireties.

What is claimed is:

1. A compound, or a pharmaceutically acceptable salt thereof, wherein the compound is:
   (1R,2S,3R)-1-(2-(5-methylisoxazol-3-yl)-1H-imidazol-5-yl)butane-1,2,3,4-tetraol;
   (1R,2S,3R)-1-(2-(5-ethylisoxazol-3-yl)-1H-imidazol-5-yl)butane-1,2,3,4-tetraol;
   (1R,2S,3R)-1-(2-(isoxazol-3-yl)-1H-imidazol-5-yl)butane-1,2,3,4-tetraol;
   (1R,2S,3R)-1-(2-(2-methylthiazol-4-yl)-1H-imidazol-4-yl)butane-1,2,3,4-tetraol;
   (1R,2S,3R)-1-(2-(1-benzyl-1H-1,2,4-triazol-3-yl)-1H-imidazol-4-yl)butane-1,2,3,4-tetraol hydrochloride;
   (1R,2S,3R)-1-(1H,1'H-2,2'-biimidazol-5-yl)butane-1,2,3,4-tetraol;
   (1R,2S,3R)-1-(2-(5-methoxy-4,5-dihydroisoxazol-3-yl)-1H-imidazol-5-yl)butane-1,2,3,4-tetraol; or
   (1R,2S,3R)-1-(2-(5-methyl-1H-pyrazol-3-yl)-1H-imidazol-5-yl)butane-1,2,3,4-tetraol.

2. A pharmaceutical composition comprising a compound of claim 1 and a pharmaceutically acceptable excipient or diluent.

* * * * *

(12) EX PARTE REEXAMINATION CERTIFICATE (7837th)
United States Patent
Augeri et al.

(10) Number: US 7,598,280 C1
(45) Certificate Issued: Oct. 26, 2010

(54) HETEROCYCLIC COMPOUNDS, COMPOSITIONS COMPRISING THEM AND METHODS OF THEIR USE

(75) Inventors: David J. Augeri, Princeton, NJ (US); Jeffrey Bagdanoff, Robbinsville, NJ (US); Simon D. P. Baugh, Ringoes, NJ (US); Kenneth G. Carson, Princeton, NJ (US); Theodore C. Jessop, Lawrenceville, NJ (US); James E. Tarver, Morrisville, PA (US)

(73) Assignee: Lexicon Pharmaceuticals, Inc., The Woodlands, TX (US)

Reexamination Request:
No. 90/010,821, Jan. 13, 2010

Reexamination Certificate for:
Patent No.: 7,598,280
Issued: Oct. 6, 2009
Appl. No.: 12/038,872
Filed: Feb. 28, 2008

Related U.S. Application Data
(60) Provisional application No. 60/904,357, filed on Mar. 1, 2007.

(51) Int. Cl.
*C07D 277/20* (2006.01)
*C07D 249/14* (2006.01)
*C07D 403/04* (2006.01)
*C07D 261/04* (2006.01)
*C07D 261/06* (2006.01)
*A61K 31/4178* (2006.01)
*A61K 31/422* (2006.01)
*A61K 31/426* (2006.01)

(52) U.S. Cl. .................. 514/365; 514/378; 514/383; 514/397; 548/205; 548/243; 548/247; 548/266.2; 548/313.4

(58) Field of Classification Search .................. None
See application file for complete search history.

(56) References Cited

U.S. PATENT DOCUMENTS

| 4,567,194 A | 1/1986 | Kroeplien |
| 2007/0208063 A1 | 9/2007 | Augeri |
| 2008/0275099 A1 | 11/2008 | Wu |
| 2009/0318516 A1 | 12/2009 | Burgoon |
| 2009/0318705 A1 | 12/2009 | Guohua |

FOREIGN PATENT DOCUMENTS

| WO | WO 97/46543 | 12/1997 |
| WO | WO 2007/002458 | 1/2007 |

OTHER PUBLICATIONS

Bagdanoff, J.T., et al., 2009, "Inhibition of Sphingosine–1–Phosphate Lyase for the Treatment of Autoimmune Disorders," *J. Med. Chem.* 52:3941–3953.
Cliff, M.D. et al., 1995, "Asymmetric Synthesis of (1R,2S, 3R)–2–Acetyl–4(5)–(1,2,3,4–tetrahydroxybutyl)imidazole," *Tetrahedron Letters* 36(33):5969–5972.
Cliff, M.D. et al., 1997, "Asymmetric Synthesis of 2–Acetyl–4(5)–1,2,3,4–tetrahydroxybutyl)imidazoles," *Journal of Organic Chemistry* 62:1023–1032.
Halweg, K.M. et al., 1985, "A Convenient Synthesis of 2–Acetyl–4(5)–(1(R),2(S),3(R),4–tetrahydroxybutyl)–imidazole," *Journal of Organic Chemistry* 50:1134–1136.
Pyne, S.G. et al., 1998, "Diastereoselective Synthesis of (1S, 2S,3R)–and (1R,2R,3R)–2–Acetyl–5–(1,2,3,4–tetrahydroxybutyl)thiazole," *Synlett* 280–282.
Pyne, S.G., 2000, "The Development of A Novel Immunosuppressive Agent Isolated From Caramel Colour III," *ACGC Chemical Research Communications* 11:108–112.
Schwab, S.R. et al., 2005, "Lymphocyte Sequestration Through S1P Lyase Inhibition and Disruption of S1P Gradients," *Science* 309:1735–1739.
PCT International Search Report and Written Opinion of the International Searching Authority dated Jul. 29, 2008, for International Application No. PCT/US2008/055210, filed Feb. 28, 2008.
European Patent Office Communication pursuant to Article 94(3) EPC dated Nov. 25, 2009, for European Application No. 08 730 902.7–2101, filed Feb. 28, 2008.
Sweeny, J.G. et al., 1985, "Synthesis of 2–Acetyl–4–(1,2,3, 4–tetrahydroxybutyl)imidazole," *Journal of Organic Chemistry* 50:1133–1134.

*Primary Examiner*—Evelyn Huang

(57) ABSTRACT

Heterocyclic compounds, compositions comprising them, and methods of their use for the treatment, prevention and management of inflammatory and autoimmune diseases and disorders are disclosed. Particular compounds are of formula I:

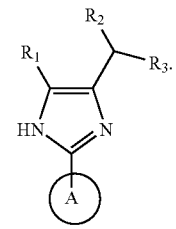

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-2 is confirmed.

* * * * *